United States Patent
Huang et al.

(10) Patent No.: US 8,953,547 B2
(45) Date of Patent: Feb. 10, 2015

(54) POWER-SAVING TDMA MAC FOR WIRELESS BODY AREA NETWORKS

(71) Applicant: Olympus Corporation, Tokyo (JP)

(72) Inventors: Rongsheng Huang, Poway, CA (US); Lichung Chu, San Diego, CA (US); Shigeyuki Shoda, San Diego, CA (US); Shinhaeng Lee, San Diego, CA (US)

(73) Assignee: Olympus Corporation, Tokyo (JP)

( * ) Notice: Subject to any disclaimer, the term of this patent is extended or adjusted under 35 U.S.C. 154(b) by 131 days.

(21) Appl. No.: 13/854,033

(22) Filed: Mar. 29, 2013

(65) Prior Publication Data

US 2014/0293850 A1    Oct. 2, 2014

(51) Int. Cl.
| | | |
|---|---|---|
| H04W 4/00 | (2009.01) | |
| H04W 52/02 | (2009.01) | |
| H04W 74/04 | (2009.01) | |
| H04J 3/00 | (2006.01) | |
| H04B 7/212 | (2006.01) | |

(52) U.S. Cl.
CPC .......... *H04W 52/0225* (2013.01); *H04W 74/04* (2013.01)
USPC ............................ 370/329; 370/280; 370/347

(58) Field of Classification Search
None
See application file for complete search history.

(56) References Cited

U.S. PATENT DOCUMENTS

| | | | |
|---|---|---|---|
| 6,597,683 B1 | 7/2003 | Gehring | |
| 7,496,059 B2 | 2/2009 | Yoon | |
| 7,742,816 B2 | 6/2010 | Masoud | |
| 7,885,240 B2 | 2/2011 | Joshi | |
| 7,995,508 B2 | 8/2011 | Ruy | |
| 8,095,812 B2 | 1/2012 | Cho | |
| 8,254,290 B2 | 8/2012 | Kim | |
| 8,265,066 B2 | 9/2012 | Prakash | |
| 8,281,408 B2 | 10/2012 | Corndorf | |
| 8,320,244 B2 | 11/2012 | Muqattash | |
| 8,320,321 B2 | 11/2012 | Joshi | |
| 8,670,435 B2* | 3/2014 | Ho | 370/348 |
| 8,750,222 B2* | 6/2014 | Falck et al. | 370/329 |
| 2011/0182222 A1 | 7/2011 | Patel | |
| 2012/0063395 A1* | 3/2012 | Ho | 370/329 |
| 2012/0063397 A1* | 3/2012 | Abedi et al. | 370/329 |
| 2012/0243454 A1* | 9/2012 | Hwang et al. | 370/311 |
| 2013/0195083 A1* | 8/2013 | Kim et al. | 370/336 |
| 2014/0133290 A1* | 5/2014 | Yokoo et al. | 370/216 |
| 2014/0198664 A1* | 7/2014 | Chen et al. | 370/241 |

OTHER PUBLICATIONS

B. Kim, J. Cho, J. Ryou, B. Lee, An Emergency Handling Scheme for Superframe-Structured MAC Protocols in WBAN, ICUIMC '11, Jan. 2011.

B. Otgonchimeg, Y. Kwon, Emergency Handling for MAC Protocol in Human Body Communication, EURASIP Journal on Wireless Communications & Networking, vol. 2011, Article ID 786903, doi: 10.1155/2011/786903, Jan. 2011.

(Continued)

*Primary Examiner* — Clemence Han
(74) *Attorney, Agent, or Firm* — Sheppard Mullin Richter & Hampton LLP

(57) ABSTRACT

A time division multiple access (TDMA) media access control (MAC) protocol is provided for wireless body area networks (BANs). In particular, in some embodiments the described network devices utilize a reservation-based power saving polling (RESP) MAC protocol for communication. The RESP MAC can be configured to provide methods for emergency event handling of both bursty data and streaming data.

38 Claims, 8 Drawing Sheets

(56) References Cited

OTHER PUBLICATIONS

S. Ullah, H. Higgins, B. Braem, etc, A Comprehensive Survey of Wireless Body Area Networks, Journal of Medical Systems, vol. 36, Issue 3, pp. 1065-1094, Jun. 2012.

H. Su, X. Zhang, Battery-Dynamics Driven TDMA MAC Protocols for Wireless Body Area Monitoring Networks in Healthcare Applications, Journal of Selected Area in Communications, vol. 27, Issue 4, pp. 424-434, May 2009.

G. Fang, E. Dutkiewicz. BodyMAC: Energy Efficient TDMA-based MAC Protocol for Wireless Body Area Networks, International Symposium on Communication and Information Technology, pp. 1455-1459, Sep. 2009.

G. Biachi, F. Borgonovo, L. Fratta, L. Musumeci, M. Zorzi. C-PRMA: A Centralized Packet Reservation Multiple Access for Local Wireless Communications, IEEE Transactions on Vehicular Technology, vol. 46, Issue 2, pp. 422-436, May 1997, OR: Global Telecommunications Conference, 1994, vol. 3, pp. 1340-1345, Nov./Dec. 1994.

Maulin Patel and Jianfeng Wang, Applications, Challenges, and Prospective in Emerging Body Area Networking Technologies, IEEE Wireless Communications, Feb. 2010.

Konrad Lorincz, David J. Malan, Thaddeus R.F. Fulford-Jones, Alan, Nawoj, Anthony Clavel, Victor Shnayder, Geoffrey Mainland, Matt Welsh. Steve Moulton. Sensor Networks for Emergency Reponse: Challenges and Opportunities, IEEE CS and IEEE ComSoc, 2004.

Ming Li and Wenjing Lou, Kui Ren, Data Security and Privacy in Wireless Body Area Networks, IEEE Wireless Communications, Feb. 2010.

Usman Mehmood, Usman Mansoor, Dong Yeop Hwang, Ki-Hyung Kim, Taekkyeun Lee, Seung Wha Yoo, Wireless Sensor Networks for Integrated Search and Rescue Efforts for Disaster Hit Areas, IEEE, ICUFN, 2012, p. 306-309.

\* cited by examiner

| Connection ID | Connection Duration | Priority | Negotiated Allocation length | Allocation Gap | In Allocation Flag (*) | Holding Time (*) | Last Allocation (*) | Allocation Adjustment (*) |
|---|---|---|---|---|---|---|---|---|
| Connection ID allocated in connection process | (in frames) | Priority specified in connection process | (in mini slot) | (in frames) | 1 or 0 | (in frames) | (in frames) | Extra mini slots applied to this connection calculated from elastic factor or due to allocation compensation |

Fig. 6

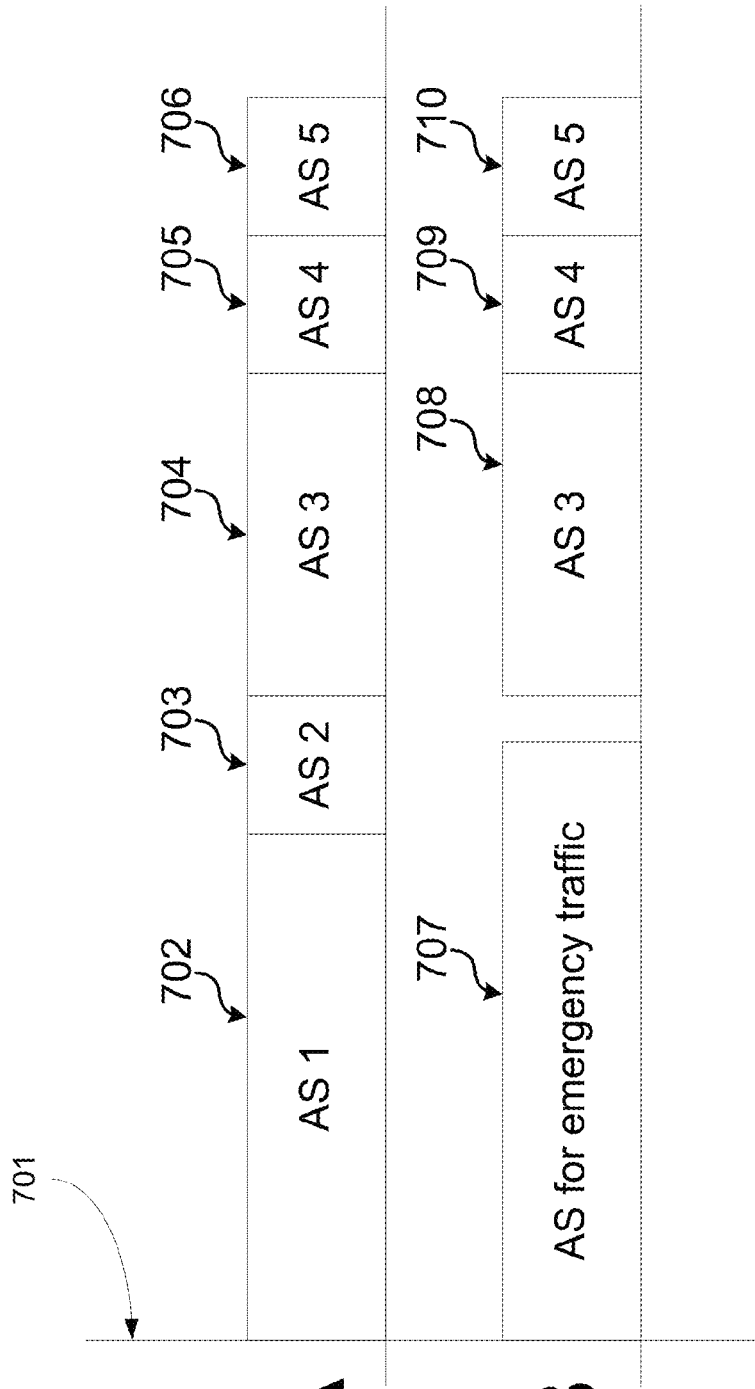

POWER-SAVING TDMA MAC FOR WIRELESS BODY AREA NETWORKS

TECHNICAL FIELD

The disclosed technology relates generally to wireless body area networks, and more particularly, some embodiments relate to systems and methods for media access control protocols for wireless body area networks.

DESCRIPTION OF THE RELATED ART

Wireless body area networks (BANs) are an emerging type of wireless network. Major targets for BANs are medical body sensors, which may be attached to or implanted in the body. Medical uses for BANs include devices that provide medical interventions, such as drug delivery devices, or pacemakers (termed "actuators").

Power consumption is a major performance consideration for BANs, particularly in the medical field. BAN devices (i.e., sensors and actuators) are typically small, with limited battery life. Additionally, recharging or changing batteries in BAN devices is often undesirable or even unpleasant to the user (for example, in an implanted medical device).

Current standards, such as IEEE 802.15.4, Bluetooth, or Bluetooth Low Energy, are not specifically designed for BANs and have unsatisfactory power consumption performance. IEEE 802.15.6 is a proposed BAN standard for use in many BAN entertainment applications and may have unsatisfactory power consumption performance in medical BANs.

Another consideration for medical BANs is the ability to handle emergencies. In some BANs, medical body sensors sense body data and upload to a real-time diagnosis center at hospital or to a cloud server for doctors' future access. A BAN's MAC is required to deliver messages for emergency events as soon as possible. Data transmitted in emergency events are expected to contain not only bursty standalone messages but also streaming data for emergency monitoring.

WPAN standards, including IEEE 802.11, 802.16, 802.15.4, and Bluetooth, do not have emergency features. IEEE 802.15.6 includes a contention-based exclusive access phase (EAP) to handle emergency events, which are assumed to be bursty traffic. In IEEE 802.15.6, it is difficult to decide the length of the EAP. If it is too short, it cannot accommodate a large amount of emergency data. If it is too long, resources are wasted for rarely occurring emergency events.

BRIEF SUMMARY OF EMBODIMENTS

A time division multiple access (TDMA) media access control (MAC) protocol is provided for wireless body area networks (BANs). In particular, in some embodiments the described network devices utilize a reservation-based power saving polling (RESP) MAC protocol for communication. The RESP MAC can be configured to provide methods for emergency event handling of both bursty data and streaming data.

Some implementations allow bi-directional traffic in the same allocation slot in a TDMA type MAC. In these implementations, there is no scheduled division of uplink traffic and downlink traffic within allocation slots. This may provide a simpler and more power saving protocol. For each frame, the hub schedules allocation slots, with each allocation slot including both uplink and downlink traffic. The hub schedules allocation slots for active connections and broadcasts the schedule to connected BAN devices, such as body sensors. Unscheduled traffic to or from connected devices can be inserted into an existing allocation slot without the need for extra reservations or contention access. This may lead to a shorter time spent awake for each connected device.

Additionally, an unreserved period may be provided for devices to build connections and associate with the network. Devices regularly having bursty traffic can use the unreserved period to transmit the bursty traffic at the price of consuming more power.

Further, a wake-up list may be appended to the end of a schedule message. The wake-up list may reduce the requirement for an unconnected device to stay awake. Sleeping devices do not need to constantly wake to check for unpredicted downlink packets. Rather, they only need to check at certain points, i.e. the wake-up list at the end of schedule messages, for potential downlink traffic. The wake-up list persists for multiple frames, so devices do not need to wake every frame to check for their ID on the wake-up list.

Moreover, in some implementations, a polling mechanism may used within the TDMA framework. Specifically, each scheduled transmission period, or allocation slot, begins with a polling message. The end of the polling message sets the start time for a polled device to transmit to the hub. This reduces the need of precise network synchronization, which is potentially power consuming. The polling messages also contain time offset information and target device address. This brings flexibility and robustness so that the hub schedule reservations in more adaptive and agile manner, thus helping body sensors to save more power. For example, unconnected devices can using the polling messages to reduce the period of time required to stay awake to search for a network beacon. By using a polling message, a waking, unconnected device does not need to remain awake continuously until it hears the next beacon. Rather, it can simply remain awake until it hears the next polling message. The device can use the time offset information to determine the length of the remainder of the frame. The device can then sleep for the determined remainder of the frame and wake up in time to hear the next beacon Implementations further include an emergency handling mechanism, which supports both streaming, monitoring-type traffic and bursty, reporting-type traffic. In the described mechanism, shorter emergency request messages or short emergency data packets are the only allowed traffic in a reserved emergency period. Accordingly, this period can be set to a very short length. Like normal traffic, emergency data can be sent in the reserved period in a continuous, connection-oriented basis. Additionally, mechanisms are provided to allow emergency data to preempt normal data in the reserved period. The emergency handling mechanism thus provides on-demand, flexible reservation duration for emergency traffic.

The emergency handling mechanism includes an association process where BAN devices' emergency reporting features are registered with the hub. This allows emergency request messages to be very short and limits the number of sensors reporting in the emergency period is limited. Therefore, the collision probability is reduced, the contention level is lowered, and the emergency connection process is expedited.

In some implementations, the polling request messages are used by the hub to allow emergency data transmissions to preempt other regular transmissions. This feature embodies a highly prioritized transmission mechanism which is highly desired by medical-oriented wireless BANs. Additionally, after an initial preemption, the emergency connection is handled according to the normal connection methods within the MAC. Accordingly, subsequent reserved allocations to emergency traffic do not interrupt other regular allocations running in parallel. The impact of emergency transmissions to other transmissions is thereby minimized.

Other features and aspects of the disclosed technology will become apparent from the following detailed description, taken in conjunction with the accompanying drawings, which illustrate, by way of example, the features in accordance with embodiments of the disclosed technology. The summary does not limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 6 illustrates an example connection table that may be maintained by the hub during BAN operation.

FIGS. 7A and 7B illustrate an example of allocation slot preemption for emergency traffic during BAN operations.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

Figure 1:
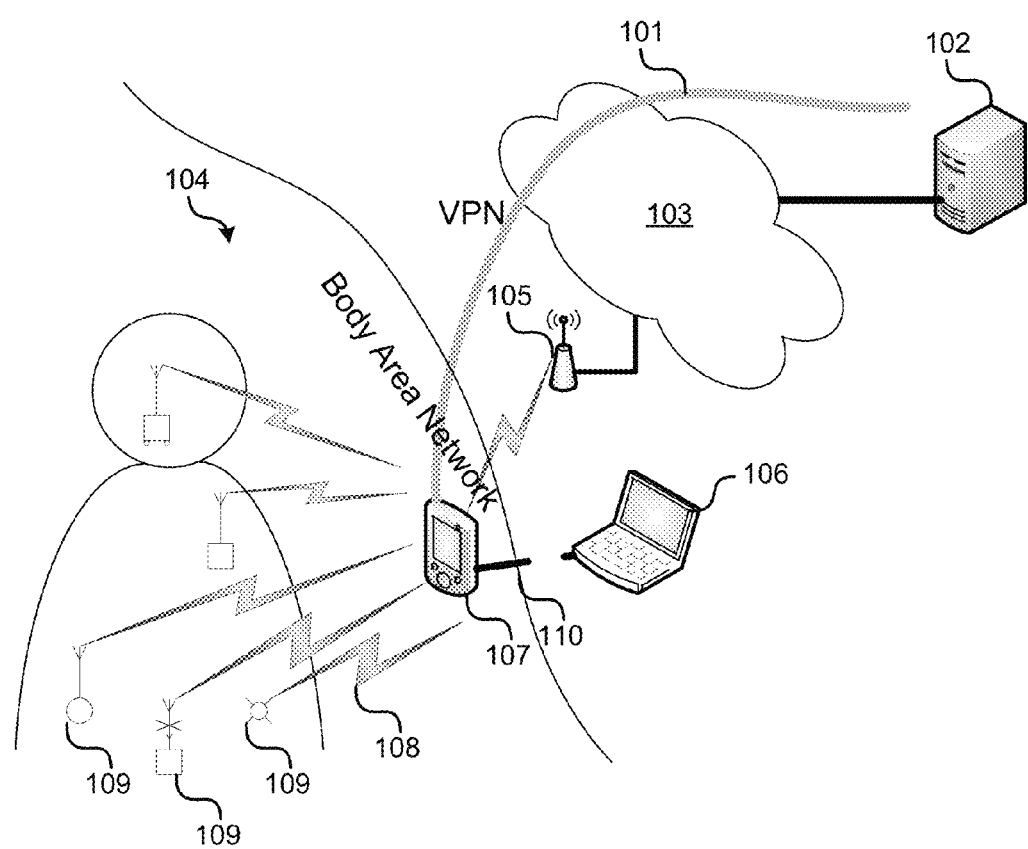
FIG. 1 illustrates an example wireless body area network (BAN).

FIG. 1 illustrates an example BAN. The BAN 104 comprises devices 109 (such as body sensors and actuators) wirelessly coupled 108 to a hub 107 in a startopology, single-hop network. The hub 107 forms a connection 101, such as a virtual private network connection (VPN), with a trusted server 102 via a wireless access point 105, such as a wireless router or cellular tower, and a network 103, such as the Internet. For example, the hub 107 may comprise a smartphone or other personal wireless device and may connect to the access point 105 via a networking protocol such as Wi-Fi or a cellular data protocol. In some implementations, the hub 107 may form a second connection 110 to a personal computer or other personal device 106—for example, through a direct connections, such as a Bluetooth connection, or through an indirect connection, such as a wireless local area network provided by access point 105.

The trusted server 102 may comprise a remote data processing center—for example, located at a hospital—where data collected by the sensors 109 is processed or stored. The server 102 may issue certain commands to the devices 109 via hub 107. However, in typical implementations, the personal device 106 is used only to access body data and is not allowed to issue commands to the devices 109.

The devices 109 usually have a relatively low data rate (in the order of 100 kbps), low duty cycle (a few minutes of active state in one day), and relatively constant connection duration (a few minutes per connection). However, bursty traffic may be supported. Additionally, the networks 104 are usually relatively stable, with devices 109 rarely joining or leaving the network 104.

Figure 2:
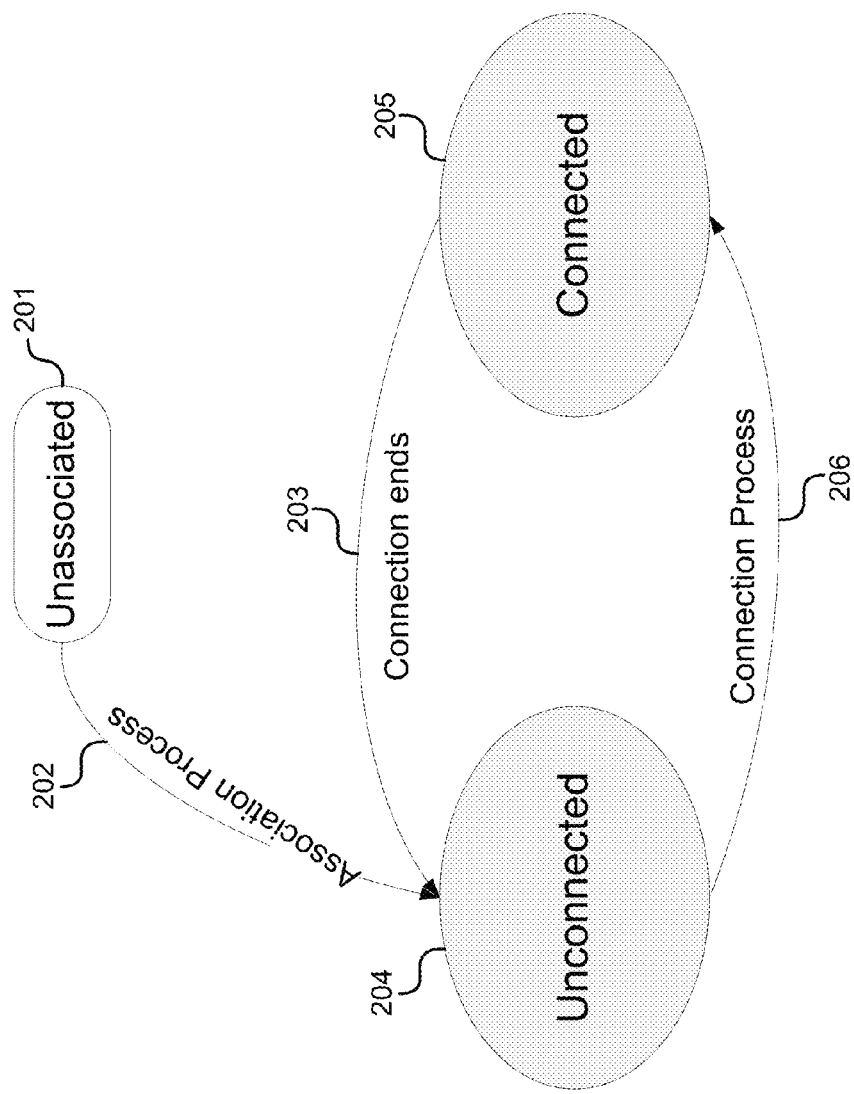
FIG. 2 illustrates various states that BAN devices may have during BAN operations.

FIG. 2 illustrates various states that BAN devices (e.g., devices 109) may have during network operations in accordance with one embodiment of the technology described herein. Each BAN device begins in an unassociated state 201. In the unassociated state 201, the BAN device is not part of the network and has not built a trust relationship with the hub or server. To join the BAN, the BAN device completes an association process 202 where the trust relationship between the hub and the BAN device is established. The association process 202 comprises transmitting an association request message from the device to the hub. Additionally, any signaling from the server required to initialize the BAN device's connection to the network can take place during the association process 202.

Additionally, devices that are able to access an emergency request period (emergency-capable devices) can register with the hub during the association process 202. Additionally, in some embodiments, emergency connection parameters are included in the association request message transmitted by the emergency-capable devices. The connection parameters set the connection requirements required to fulfill the BAN device's emergency operations. For example, if the BAN device's emergency operational requirements entail reporting bursty or continuous monitoring data to the server, the emergency connection parameters may specify the connection required to provide such reporting. The emergency connection parameters may include, for example, (a) emergency connection length requirements, (b) the size and frequency of allocations during the emergency connection, and (c) whether the emergency connection will require a continuous period of monitoring. In other cases, the BAN device may not have data to report during emergency operation—for example, the BAN device may simply issue an alarm. In these cases, the emergency connection parameters may reflect that no emergency connection is needed and that the hub should transmit an alert to the server when it receives an emergency message from the BAN device.

Once the BAN device associates with the network 202, the BAN device is in an unconnected state 204. In the unconnected state 204, the BAN device retains an association with the network, including the trust relationship with the hub. For example, once the device is in the unconnected state 204 session keys can be generated and exchanged without signaling from the server. A device in the unconnected state 204 is typically asleep. However, in some cases, the device may use an unreserved communication period (discussed below) to communicate with the hub while in the unconnected state 204. The hub assumes that a device in the unconnected state 204 is asleep, and will not schedule downlink packets for an unconnected device. Instead, if there is a downlink packet pending, the hub posts the device's ID in a wakeup list (described below).

When the device has data to transmit to the hub, it performs a connection process 206 to enter a connected state 205. For example, the device may enter the connected state 205 to transmit a sensor report to the server via the hub or to receive packets from the server via the hub. As another example, the device may enter the connected state 205 to transmit an emergency message. The connection process 206 used to enter connected state 205 may depend on whether or not the device has emergency data. The connected state 205 is the state in which a device has its transmission and reception scheduled by the hub. After the scheduled traffic has completed, the connection ends 203 and the device re-enters the unconnected state 204.

Figure 3:
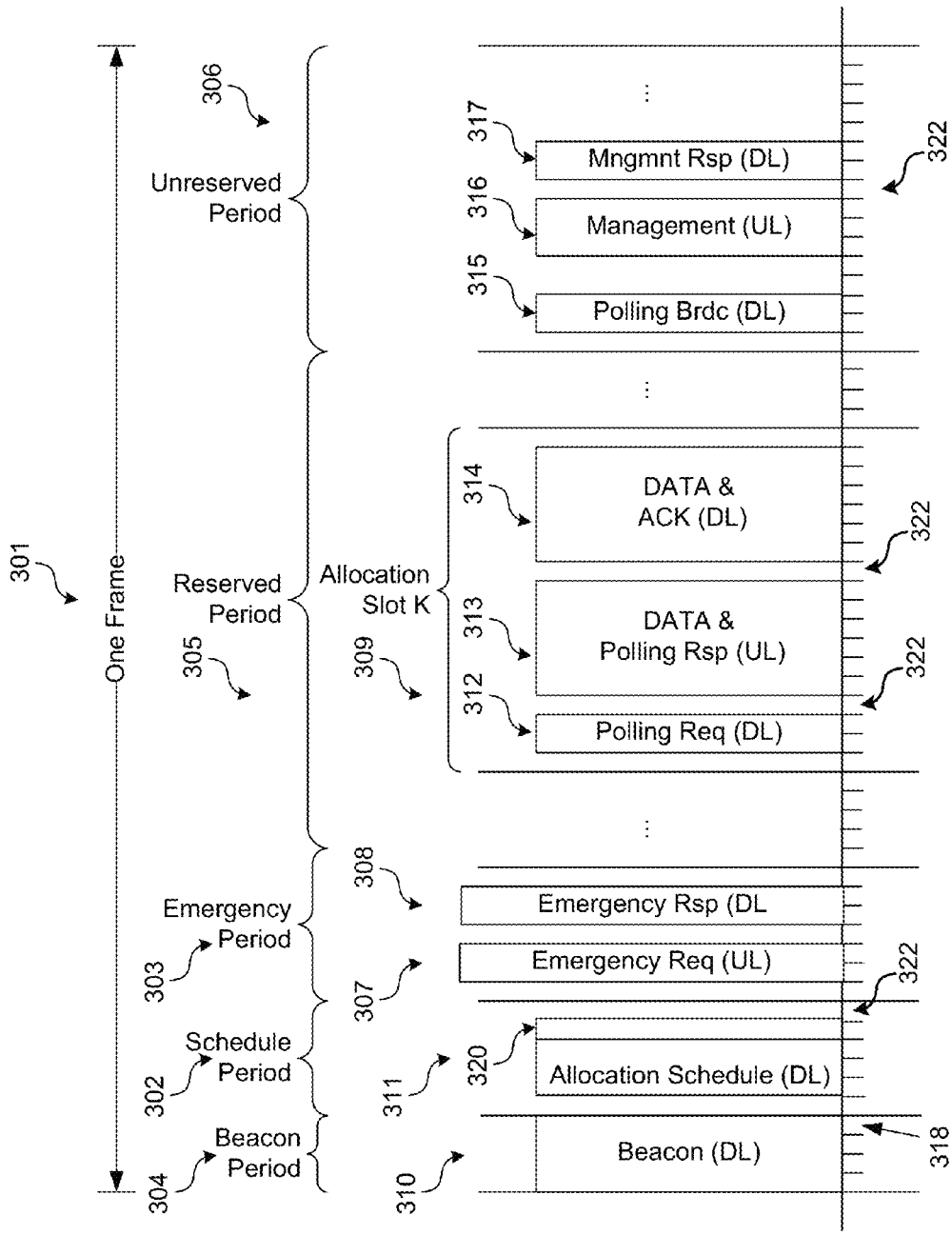
FIG. 3 illustrates an example frame structure for BAN operations.

FIG. 3 illustrates an example frame structure for use in a BAN in accordance with one embodiment of the technology described herein. Communications in some implementations utilize time-division multiple access (TDMA) for channel access in the BAN. The BAN frequency channel is divided into timeslots 318, which are grouped into frames 301. Transmissions in the frame 301 are separated by at least one short inter-frame spacing (SIFS) period 322.

The frame 301 begins with a beacon period 304 where the hub broadcasts a beacon 310. The beacon 310 may contain various information, such as, for example, (a) frame synchronization and timing information; (b) BAN information, such as the BAN ID; (c) channel information; and (d) the length of the frame.

In the illustrated example, scheduling period 302 takes place after the beacon period 304. The hub broadcasts an allocation schedule message 311 during the schedule period 302. The allocation schedule message 311 sets the division between the reserved period 305 and the unreserved period 306. The reserved period 305 is used to communicate with devices in a connected state. The unreserved period 306 is used to communicate with devices in an unconnected state and to communicate with devices in an unassociated state.

The allocation schedule message 311 can include a schedule of which BAN devices reserved allocation slots 309 during the reserved period 305. In some implementations, the allocation schedule message 311 includes the start times of all reserved allocation slots 309. This may be used by the BAN devices to determine the length of their reserved allocation slots 309. In other implementations, the allocation schedule message 311 includes the lengths of the reserved allocation slots 309. In still further implementations, the allocation slots 309 have a fixed length and the allocation schedule message 311 can include an ordered list of BAN devices. In some implementations, the allocation schedule message 311 can further includes a start time of the unreserved period 306. For example, the allocation schedule message 311 may include the start time of the unreserved period 306 if it is not calculable from the other information in the allocation schedule message 311.

The allocation schedule message 311 can further include a wake-up list 320. The wake-up list 320 comprises a list of unconnected BAN devices that have waiting downlink packets. An unconnected BAN device is listed in the wake-up list 320 in consecutive frames 301 until the BAN device builds a connection. In some implementations, the hub may have an expiration timer where an unconnected BAN is dropped from the wake-up list 320 after a certain number of frames. The wake-up list 320 allows BAN devices to remain asleep in an unconnected state for long periods. Even if a BAN device may receive unpredictable downlink traffic, there is no need for the device to check for downlink traffic every frame. Rather, the device may only check the wake-up list 320 periodically because the device will remain on the wake-up list 320 until it builds a connection.

In the illustrated example, an emergency period 303 occurs after the scheduling period 302. The BAN devices that have registered as emergency-capable during the association process 202 (FIG. 2) may use the emergency period 303. In implementations where the emergency period 303 occurs immediately after the schedule period 302, devices can access the channel immediately after listening to the beacon 310 and allocation schedule message 311. This reduces the latency need to synchronize with the hub when an emergency event occurs.

Communication during the emergency period 303 can include emergency request messages 307 transmitted by emergency-capable devices and emergency request response messages 308 transmitted by the hub. In some cases, an emergency request message 307 indicates that the hub should build a connection 206 (FIG. 2) according to the emergency connection parameters set during the association process 202 (FIG. 2). Because the emergency connection parameters can be set during association process 202 (FIG. 2), the emergency request messages 307 may be shorter than the connection request messages 316 (discussed below).

In other cases, the emergency-capable device does not need an emergency connection—for example, if the emergency-capable device simply transmits an emergency signal or short emergency data packet as the emergency request 307. In these cases, the hub may relay the emergency event to the server upon receiving the emergency request message 307. In further implementations, emergency event signaling or data packets can be included as part of the emergency request message 307 to build an emergency connection.

The emergency response 308 can be included to provide a receipt acknowledgement to the device from the hub. The emergency response 308 may also include a confirmation that the emergency connection parameters set during the association process 202 (FIG. 2) will be followed. If the emergency connection parameters will not be followed, the emergency response 308 may further include finalized values of the connection parameters. Additionally, as described below, when an emergency request 307 is transmitted, normally scheduled allocation slots 309 in the frame may be preempted to begin the emergency connection. The emergency response message 308 may include a schedule for the preempted allocation slot 309 that will be used for the first slot of the emergency connection. Allocation slots 309 during future frames of the emergency connection (i.e., frames after the one in which the emergency request 307 was transmitted) are scheduled normally and are included in the allocation schedule message 311.

The length of the emergency period 303 can be fixed by the BAN's MAC protocol. Typically, the emergency period 303 will be used only rarely. When it is not in use, the BAN can be idle. Accordingly, the length is preferably short enough to avoid unnecessary waste of channel resources. For example, the emergency period 303 may be short enough for only one, two, or three emergency request 307 and response 308 exchanges.

The access method used by the emergency-capable devices to access the emergency period 303 may differ between BANs. For example, if the number of emergency-capable devices is less or equal to the number of potential emergency request messages 307, the BAN may use a reservation-based access method. Here, the BAN may reserve specific periods within the emergency period 303 for specific emergency-capable devices.

If the number of emergency-capable devices exceeds the number of potential request messages 307, the BAN may use a contention-based access method. Here, the emergency-capable devices use a contention method to access the channel during emergency period 303. For example, the emergency-capable devices may use slotted ALOHA, carrier sense multiple access with collision avoidance (CSMA/CA), p-persistent ALOHA, or p-persistent CSMA to access the channel. Because emergency events are likely to be rare, collisions to access the channel during emergency period 303 are also likely to be rare.

In some implementations, the access method to be used is provided in the beacon 310. If the access method changes during network operation, the hub can update the beacon 310.

In still further implementations, the emergency period 303 access method is fixed. For example, contention based access may always be used to access the emergency period 303, regardless of the number of BAN devices In the illustrated example, reserved period 305 occurs after the emergency period 303. The reserved period 305 can include one or more allocation slots 309. Each allocation slot 309 can be reserved for a different connected device. Additionally, in some implementations, the hub may reserve one or more allocation slots 309 for non-existent (dummy) devices to allow the hub device to sleep. In some implementations, each allocation slot 309 has a set size. In other implementations, the allocation slots 309 may have different sizes—for example, depending on the connection requirements.

An allocation slot 309 is begun by a polling request message 312 transmitted by the hub. BAN devices may sleep after receiving the allocation schedule message 311 until the start time of their scheduled allocation slot 309. Some resynchronization may occur during this sleep period. Accordingly, the BAN devices are programmed to wake up at least one guard time interval before their scheduled allocation slot 309. The guard time takes into account probable synchronization loss and is configured to cause the devices to wake a sufficient time before their allocation slot 309 to receive the polling request message 312.

Each polling request 312 can include a device address for the device allowed to transmit during the allocation slot 309. In some cases, the device address in the polling request 312 may not match the device scheduled to use the allocation slot 309 as indicated in the allocation schedule message 311. For example, this may occur if a BAN device's allocation slot 309 has been preempted for an emergency allocation slot.

A BAN device transmits to the hub after receiving a polling request message 312 addressed to the device. Accordingly, the device does not need to maintain an accurate network synchronization to become aligned with its allocation slot 309. Thus, in some embodiments the device can sleep between the allocation schedule message 311 and the allocation slot 309 without maintaining precise network synchronization and without requiring re-synchronization when waking.

The polling request message 312 may further include relative time offset, for example, the relative time offset information may comprise the current timeslot 318 position of the allocation slot 309. Other BAN devices, such as unconnected devices waking up to use the unreserved period 306 to build a connection, may use the time offset information contained in the polling request messages 312 to align to the network timing. This alignment may be used to reduce the time spent by unconnected device to search for the beacon 310. For example, if an unconnected device wakes up during after the reserved period 305, the unconnected device can listen to the next polling request message 312 to determine the current timeslot of the frame 301. The unconnected device can use this information to determine the time remaining in the current frame 301. The unconnected device may then reenter a sleep state for the remainder of the frame 301 and wake up in time to hear the next beacon 310. Accordingly, the polling request messages 312 provides power-saving to unconnected devices because they may be used by waking, unconnected devices to avoid having to remain awake until the next beacon 310.

The polling request message 312 may further include the duration of the allocation slot 309 (if the duration is not fixed during network operations), and the BAN device ID of the device able to use the allocation slot 309. If the allocation slot 309 has been preempted by an emergency request 307, the BAN device ID in the polling request message 312 can be configured to differ from the BAN device ID scheduled in the allocation schedule message 311.

After a SIFS 322, the device identified in the polling request message 312 (the polled device) transmits an uplink response 313, comprising an uplink data packet or a polling response message indicating no uplink data. After the response 313, the hub transmits a downlink response 314. The downlink response 314 comprises an acknowledgement (ACK) of the uplink data packet (if transmitted) and a downlink data packet (if the hub has downlink data). In some implementations, each allocation slot 309 may have more than one packet exchange 313, 314. Subsequent uplink packets 313 include an ACK for the previous downlink data packet 314.

There is no set division between uplink traffic 313 and downlink traffic 314 during an allocation slot 309. This reduces complexity and allows devices to sleep more often. Rather the allocations schedule message 311 simply schedules the start time (and, in some cases, length) of the allocation slot 309.

The polled device may reenter a sleep state after the last downlink response 314. If the messages 313 and 314 do not take up the entire allocation slot 309, the hub may also sleep for the remainder of the allocation slot 309. Additionally, if the polled device does not transmit a response 313, the hub can use the allocation slot 309 to sleep.

The reserved period 305 ends after the last scheduled allocation slot 309. Accordingly, the length of the reserved period 305 can be configured to vary between consecutive frames 301. Additionally, in some embodiments, the reserved period 305 may not occur in a frame 301 if no allocation slot 309 is scheduled for the frame 301.

An unreserved period 306 occurs after the reserved period 305 (or after the emergency period 303, if there is no reserved period 305). In some embodiments, the reserved period 305 has a maximum length to ensure that there is a predetermined minimum length for the unreserved period 306.

BAN devices use the unreserved period 306 to build a connection with the hub or to transmit bursty uplink data to the hub. Additionally, new network devices begin (or conduct) the association process 202 (FIG. 2) during the unreserved period 306. Devices may also use the unreserved period 306 to rebuild lost connections or change connection parameters. Furthermore, emergency-capable devices may use the unreserved period 306 in the same manner as the emergency period 303.

The BAN devices can be configured to use a convention-based access mode to access the channel during the unreserved period 306. For example, the contention-based access mode may be slotted ALOHA, CSMA/CA, p-persistent ALOHA, or p-persistent CSMA. The contention based-access mode during the unreserved period 306 may be the same or different than the one used during the emergency period 303 (if one is used during the emergency period 303).

The unreserved period 306 in this example begins with a polling broadcast message 315 broadcast by the hub. In some implementations, a broadcasting destination address (broadcasting ID) is established. The polling broadcast message 315 (and other broadcast messages 310, 311) may use the broadcasting ID.

Devices that woke in time to receive the beacon 310 and allocation schedule message 311, will know the start time of the unreserved period 306 form the allocation schedule message 311. They may then sleep a short time during the reserved period 305 and wake up in time to receive the polling broadcast message 315. Like the scheduled devices, the unconnected devices waking for the unreserved period 306 may wake a predetermined guard interval before the polling broadcast message 315. While they may lose some network synchronization during the short sleep, they can rely on the end of polling broadcast message 315 to begin transmitting.

The polling broadcast message 315 may also include timing information (such as the starting timeslot of the unreserved period 306) to allow devices waking from an unconnected state to synchronize to the network.

Devices can be configured to transmit uplink management messages 316 to the hub. These uplink management messages 316 may comprise connection request messages, emergency connection request messages, emergency reporting messages, uplink data packets, association requests, and other management messages. In response, to a received uplink message 316, the hub responds with an appropriate management response 317, such as a connection request response, an emergency connection response, an ACK of an uplink data packet, an association response, or responses to other management messages.

An emergency request message sent during the unreserved period 306 may be similar to an emergency request message 307 sent during an emergency period 303. In some implementations, during the unreserved period 306, emergency request messages are given a higher priority than other messages 316. For example, a shorter inter-frame spacing 322 or smaller contention window size may be used for emergency request messages.

Figure 4:
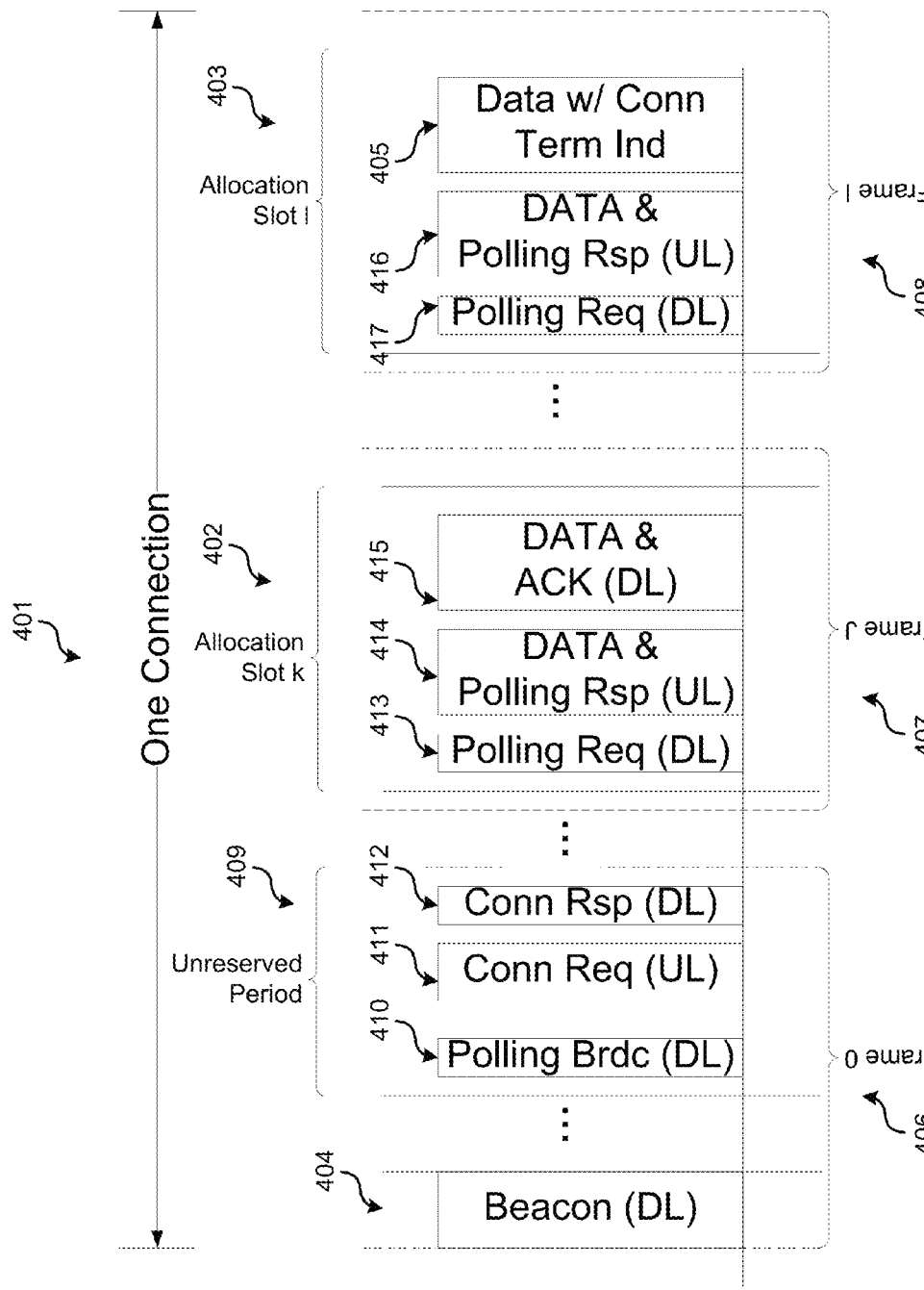
FIG. 4 illustrates an example connection for a BAN device during BAN operations.

FIG. 4 illustrates the life span of a connection 401 between a hub and a connected device in accordance with one embodiment of the technology described herein. The connection in this example comprises a first frame 406 where the connection is built and subsequent frames 407, 408 where communication takes place during corresponding allocation slots 402, 403. In some implementations, the number of frames between connection frames 407, 408 may vary depending on connection. For example, a connection, such as an emergency connection for a monitoring device, may have an allocation slot 402, 403, scheduled every frame. Another connection may have allocation slots 402, 403 scheduled every other, every third, or every nth frame.

The example connection 401 begins during the unreserved period 409 of a first frame 406. The device building the connection uses the beacon period 404 (or a polling message 312, 315 (FIG. 3) to synchronize to the network timing. During the unreserved period 409 of frame 406, the device listens to the polling broadcast 410 and exchanges a connection request 411 and response 412 with the hub. For non-emergency connections, the connection request 411 and response 412 are used to set the connection parameters for the connection 401. Connection parameters may include the duration of the connection 401, number of frames between allocation slots 402, 403, the data rate used during the connection, priority, traffic direction, allocation slot 402, 403, durations, whether encryption will be used, and other connection parameters. For emergency connections, the connection parameters are set during the association process and the connection request 411 and connection response 412 are used to set up a connection 401 according to these predetermined connection parameters.

During the subsequent frames 407, 408 of the connection 401 (typically the frame immediately after the first frame 406), the device may have allocation slots 402, 403 scheduled for it. As discussed above, the allocation slots 402, 403, can include polling requests 413, 417; uplink data or polling response messages 414, 416; and ACK or downlink messages 415, 405.

Additionally, the last downlink message 405 may include a connection termination indication. In some implementations, the connection 401 length is extended in certain circumstances. For example, the connection 401 may be extended if unexpected uplink or downlink traffic is generated during the connection, or if one or more allocation slots 402, 403 are preempted by an emergency connection. In these implementations, the device will continue listening to schedules (at the frame frequency between allocation slots 402, 403) until the downlink message 405 with connection termination indicated.

Figure 5:
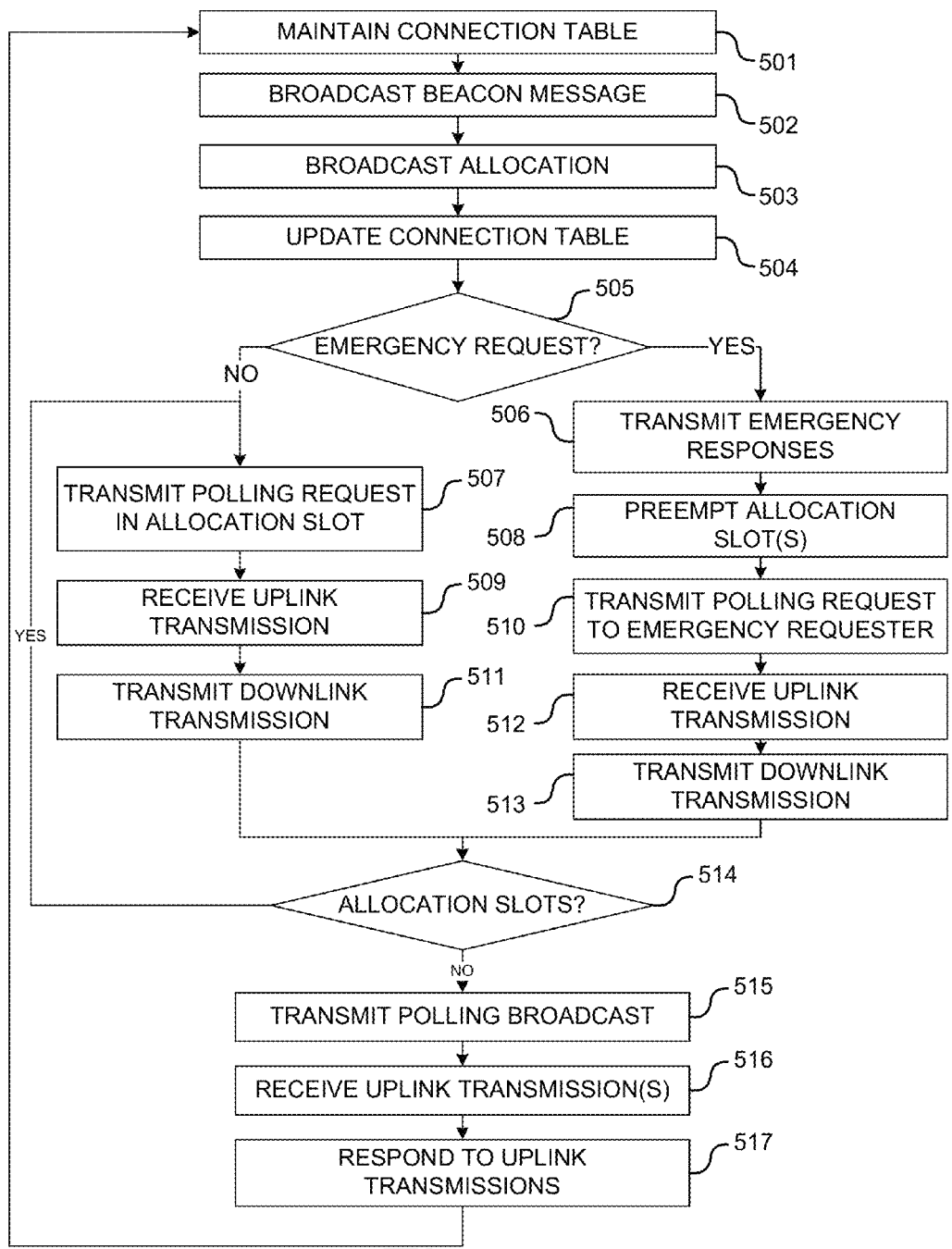
FIG. 5 illustrates an example of hub operations during BAN operation.

FIG. 5 illustrates a method of network operation in accordance with one embodiment of the technology described herein. The hub maintains a connection table 501 to schedule allocation slots for BAN devices. For each new connection, the step 501 comprises the hub adding an entry to the connection table. An example connection table is presented in FIG. 6. Each entry of the connection table includes: (a) a connection ID; (b) the connection duration as a number of frames; (c) the connection priority; (d) the negotiated allocation slot length as a number of timeslots; (e) the number of frames between allocation slots; (f) an in-allocation flag field; (g) a holding time as a number of frames; (h) the number of frames since the last allocation slot; and (i) an allocation adjustment as a number of timeslots. Certain entries of the allocation table may be set during the connection process (for emergency connections, during the association process), such as the connection ID, connection duration, connection priority, negotiated allocation slot length, and number of frames between allocation slots. Additionally, in certain implementations, emergency connections are assigned a highest connection priority unavailable to non-emergency connections.

After a frame ends, during step 501, the hub sorts the connection table by priority. Connections with higher priorities are given allocations 309 (FIG. 3) preferentially. After sorting, the hub uses the allocation gap and last allocation information to determine if a connection needs an allocation in the coming frame. The hub updates the in-allocation flag to 1 if a connection needs an allocation in the coming frame.

Next, as part of step 501, the hub fulfills the allocation for the connections with in-allocation flag equal 1. The allocation information can be stored in the hub in a format similar to the allocation schedule message 311 (FIG. 3). If the total allocation slots needed to fulfill the needed connections exceeds the available time of the reserved period 305, then allocations for connections with lower priorities are not fulfilled. The unfulfilled allocation lengths are added to the unfulfilled connection's allocation adjustment field. If the total allocation does not exceed the length of the available reserved period 305 (FIG. 3) length, then the hub may allocate an empty allocation slot before the unreserved period 306 to save power.

In step 502, the hub starts the current frame by broadcasting the beacon message 310 (FIG. 3). In step 503, the hub broadcasts the allocation schedule determined during step 501. After transmitting the beacon 502 or the allocation schedule 503, the hub updates the connection table 504 by adding one frame to the holding time and last allocation fields for all entries.

Next, the hub listens during the emergency period to determine if there are any emergency requests 505. If the hub hears an emergency request, the hub transmits an emergency response 506 and builds an emergency connection (which may include updating the connection table).

As part the first frame of the emergency connection, the hub preempts 508 one or more of the first allocation slots of the reserved period to build an emergency allocation slot. FIGS. 7A and 7B illustrate an example of preemption 508. Referring now to FIGS. 7A and 7B, at the beginning 701 of the current frame's reserved period, a plurality of allocation slots 702, 703, 704, 705, 706 are scheduled. In this example, during the association process, the emergency connection had a negotiated allocation length greater than the length of allocation 702. Accordingly, both allocation slots 702 and 703 are preempted and an emergency allocation slot 707 is provided for the emergency-requesting device. Allocation slots 708, 709, 710 proceed as scheduled. During step 508, if a connection has its allocation slot preempted, the length of the preempted allocation is added to the preempted device's allocation adjustment entry.

Returning to FIG. 5, in step 510, the hub begins the emergency allocation slot 707 by transmitting a polling request to the emergency requester. The polling request transmitted in step 510 can include the device ID of the emergency requester, not the device that was originally scheduled slot 702. The hub may then receive uplink emergency transmissions 512 from the emergency requester and provides any required downlink traffic 513, including ACKs.

If an emergency request is not received 505, then the hub transmits a polling request 507 to the first scheduled device to begin the first scheduled allocation slot. The allocation slot proceeds with the hub receiving uplink traffic 509 and transmitting downlink traffic 511 to the scheduled device.

In both cases 505, at the end of each allocation slot, the hub clears the in-allocation flag and updates the last allocation field, and if necessary, the adjustment field. If the hub uses the current allocation slot for extra management messages, it also adds compensation to the adjustment field. During subsequent scheduling 501, the adjustment allocation decreases only after the holding time reaches the connection duration. When the adjustment allocation reaches 0, the hub terminates the connection.

After the scheduled (or emergency) allocation slot, the hub repeats 514 for the remaining scheduled allocation slot(s) (and the remaining emergency allocation slot(s), if multiple emergency requests were received).

After 514 the reserved period, the hub begins the unreserved period by transmitting the polling broadcast message 515. Then, during the unreserved period, the hub receives 516 and responds 517 to any uplink transmissions.

Figure 8:
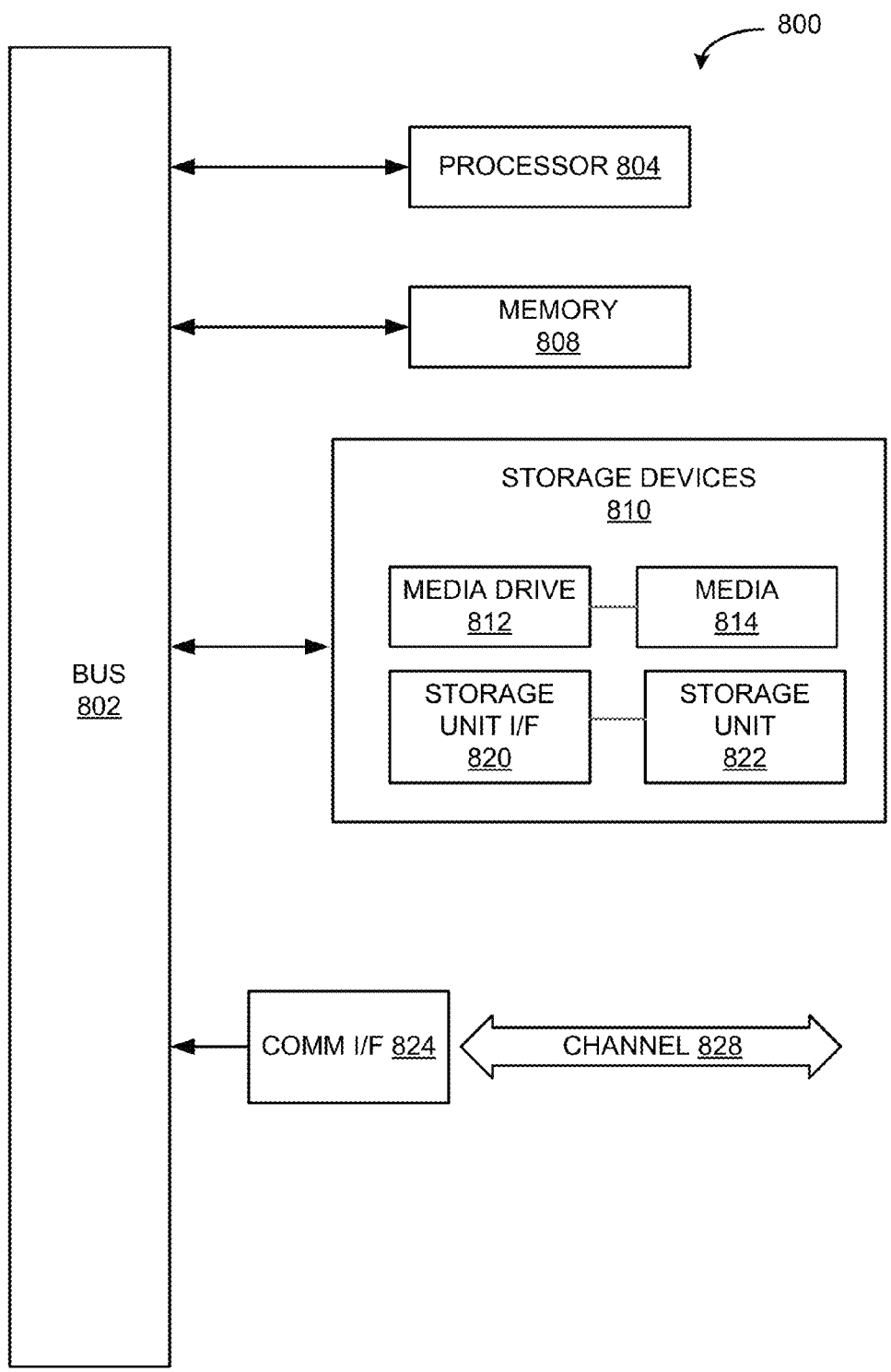
FIG. 8 illustrates an example computing module that may be used in implementing various features of embodiments of the disclosed technology.

As used herein, the term module might describe a given unit of functionality that can be performed in accordance with one or more embodiments of the technology disclosed herein. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the technology are implemented in whole or in part using software, in one embodiment, these software elements can be implemented to operate with a computing or processing module capable of carrying out the functionality described with respect thereto. One such example computing module is shown in FIG. 8. Various embodiments are described in terms of this example-computing module 800. After reading this description, it will become apparent to a person skilled in the relevant art how to implement the technology using other computing modules or architectures.

Referring now to FIG. 8, computing module 800 may represent, for example, computing or processing capabilities found within desktop, laptop and notebook computers; handheld computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 800 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 800 might include, for example, one or more processors, controllers, control modules, or other processing devices, such as a processor 804. Processor 804 might be implemented using a general-purpose or special-purpose processing engine such as, for example, a microprocessor, controller, or other control logic. In the illustrated example, processor 804 is connected to a bus 802, although any communication medium can be used to facilitate interaction with other components of computing module 800 or to communicate externally.

Computing module 800 might also include one or more memory modules, simply referred to herein as main memory 808. For example, preferably random access memory (RAM) or other dynamic memory, might be used for storing information and instructions to be executed by processor 804. Main memory 808 might also be used for storing temporary variables or other intermediate information during execution of instructions to be executed by processor 804. Computing module 800 might likewise include a read only memory ("ROM") or other static storage device coupled to bus 802 for storing static information and instructions for processor 804.

The computing module 800 might also include one or more various forms of information storage mechanism 810, which might include, for example, a media drive 812 and a storage unit interface 820. The media drive 812 might include a drive or other mechanism to support fixed or removable storage media 814. For example, a hard disk drive, a floppy disk drive, a magnetic tape drive, an optical disk drive, a CD or DVD drive (R or RW), or other removable or fixed media drive might be provided. Accordingly, storage media 814 might include, for example, a hard disk, a floppy disk, magnetic tape, cartridge, optical disk, a CD or DVD, or other fixed or removable medium that is read by, written to or accessed by media drive 812. As these examples illustrate, the storage media 814 can include a computer usable storage medium having stored therein computer software or data.

In alternative embodiments, information storage mechanism 810 might include other similar instrumentalities for allowing computer programs or other instructions or data to be loaded into computing module 800. Such instrumentalities might include, for example, a fixed or removable storage unit 822 and an interface 820. Examples of such storage units 822 and interfaces 820 can include a program cartridge and cartridge interface, a removable memory (for example, a flash memory or other removable memory module) and memory slot, a PCMCIA slot and card, and other fixed or removable storage units 822 and interfaces 820 that allow software and data to be transferred from the storage unit 822 to computing module 800.

Computing module 800 might also include a communications interface 824. Communications interface 824 might be used to allow software and data to be transferred between computing module 800 and external devices. Examples of communications interface 824 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 824 might typically be carried on signals, which can be electronic, electromagnetic (which includes optical) or other signals capable of being exchanged by a given communications interface 824. These signals might be provided to communications interface 824 via a channel 828. This channel 828 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 808, storage unit 820, media 814, and channel 828. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 800 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A method, comprising:
a hub device scheduling an allocation slot for uplink and downlink communications with a network device;

the hub device transmitting a scheduled start time of the allocation slot to the network device;

during the allocation slot, the hub device receiving uplink data from the network device; and at an unscheduled time after receiving the uplink data and during the allocation slot, the hub device transmitting downlink data to the network device.

2. The method of claim 1, further comprising:

during the allocation slot before receiving uplink data from the network device, the hub device transmitting a polling request to the network device.

3. The method of claim 2, wherein the polling request comprises timing information about the timeslot of the scheduled start time for the allocation period.

4. The method of claim 3, wherein the polling request comprises a destination address for the network device.

5. The method of claim 3, wherein the polling request comprises a duration of the allocation slot.

6. The method of claim 1, further comprising transmitting a wake-up list during a scheduled wake-up list transmission period.

7. The method of claim 6, wherein the wake-up list comprises a list of associated and unconnected network devices having waiting downlink traffic.

8. The method of claim 1, further comprising scheduling an unreserved period to occur after the allocation slot.

9. The method of claim 8, further comprising transmitting a polling broadcast message at the beginning of the unreserved period.

10. The method of claim 1, further comprising maintaining a connection table of connected and associated network devices.

11. The method of claim 1, further comprising transmitting an unscheduled downlink packet during the unscheduled time after receiving the uplink data and the allocation slot.

12. The method of 1, further comprising receiving an unscheduled uplink packet as the uplink data.

13. A method, comprising:

a network device receiving a scheduled start time of an allocation slot from a hub device;

during the allocation slot, the network device transmitting uplink data to the hub device; and at an unscheduled time after transmitting the uplink data and during the allocation slot, the network device receiving downlink data from the hub device.

14. The method of claim 13, further comprising:

during the allocation slot and before transmitting uplink data to the hub device, the network device receiving a polling request from the hub device.

15. The method of claim 14, wherein the polling request comprises timing information about a timeslot of the scheduled start time for the allocation period; a destination address for the network device; and a duration of the allocation slot.

16. The method of claim 13, further comprising, before receiving the scheduled start time:

the network device associating with the hub device;

the network device entering an unconnected state with the hub device;

the network device receiving a wake-up list broadcast from the hub device; and the network device entering a connected state with the hub device.

17. The method of claim 16, wherein the step of entering the connected state with the hub device takes place during a scheduled unreserved period.

18. The method of claim 16, wherein, during the connected state, the network device receives subsequent scheduled start times of subsequent allocation slots during non-contiguous frames, and wherein the network device sleeps during one or more intervening frames between two sequential frames of the non-contiguous frames.

19. The method of claim 16, further comprising the network device entering the unconnected state after the allocation period.

20. The method of claim 13, further comprising:

the network device entering a sleep state after receiving the scheduled start time of the allocation slot; and the network device waking from the sleep state at a guard interval before the scheduled start time of the allocation slot.

21. A network device programmed to perform a method of network communication, the method comprising:

a hub device scheduling an allocation slot for uplink and downlink communications with a network device;

the hub device transmitting a scheduled start time of the allocation slot to the network device;

during the allocation slot, the hub device receiving uplink data from the network device; and at an unscheduled time after receiving the uplink data and during the allocation slot, the hub device transmitting downlink data to the network device.

22. The network device of claim 21, the method further comprising:

during the allocation slot before receiving uplink data from the network device, the hub device transmitting a polling request to the network device.

23. The network device of claim 22, wherein the polling request comprises timing information about timeslot of the scheduled start time for the allocation period, a destination address for the network device, and a duration of the allocation slot.

24. The network device of claim 21, the method further comprising transmitting a wake-up list during a scheduled wake-up list transmission period.

25. The network device of claim 24, wherein the wake-up list comprises a list of associated and unconnected network devices having waiting downlink traffic.

26. The network device of claim 21, the method further comprising scheduling an unreserved period to occur after the allocation slot.

27. The method of claim 26, the method further comprising transmitting a polling broadcast message at the beginning of the unreserved period.

28. The network device of claim 21, the method further comprising maintaining a connection table of connected and associated network devices.

29. The network device of claim 21, the method further comprising transmitting an unscheduled downlink packet during the unscheduled time after receiving the uplink data and the allocation slot.

30. The network device of claim 21, the method further comprising receiving an unscheduled uplink packet as the uplink data.

31. A network device programmed to perform a method of network communication, the method comprising:

a network device receiving a scheduled start time of an allocation slot from a hub device;

during the allocation slot, the network device transmitting uplink data to the hub device; and at an unscheduled time after transmitting the uplink data and during the allocation slot, the network device receiving downlink data from the hub device.

32. The network device of claim 31, the method further comprising:

during the allocation slot and before transmitting uplink data to the hub device, the network device receiving a polling request from the hub device.

33. The network device of claim 32, wherein the polling request comprises timing information about timeslot of the scheduled start time for the allocation period; a destination address for the network device; and a duration of the allocation slot.

34. The network device of claim 31, the method further comprising, before receiving the scheduled start time:
- the network device associating with the hub device;
- the network device entering an unconnected state with the hub device;
- the network device receiving a wake-up list broadcast from the hub device; and
- the network device entering a connected state with the hub device.

35. The network device of claim 34, wherein the step of entering the connected state with the hub device takes place during a scheduled unreserved period.

36. The network device of claim 34, wherein, during the connected state, the network device receives subsequent scheduled start times of subsequent allocation slots during non-contiguous frames, and wherein the network device sleeps during one or more intervening frames between two sequential frames of the non-contiguous frames.

37. The network device of claim 34, the method further comprising the network device entering the unconnected state after the allocation period.

38. The network device of claim 31, the method further comprising:
- the network device entering a sleep state after receiving the scheduled start time of the allocation slot; and
- the network device waking from the sleep state at a guard interval before the scheduled start time of the allocation slot.

* * * * *